US012311420B2

(12) United States Patent
West

(10) Patent No.: US 12,311,420 B2
(45) Date of Patent: *May 27, 2025

(54) SYSTEM AND METHOD FOR VERTICALLY-ORIENTED COMPOSTING

(71) Applicant: NextGen Organics, Port Orchard, WA (US)

(72) Inventor: Jeffrey West, Port Orchard, WA (US)

(73) Assignee: NextGen Organics, Inc., Port Orchard, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/496,516

(22) Filed: Oct. 27, 2023

(65) Prior Publication Data

US 2024/0246129 A1 Jul. 25, 2024

Related U.S. Application Data

(63) Continuation of application No. 18/301,235, filed on Apr. 16, 2023, now Pat. No. 11,858,016.

(60) Provisional application No. 63/440,917, filed on Jan. 25, 2023.

(51) Int. Cl.
| | |
|---|---|
| *B09B 3/70* | (2022.01) |
| *B09B 3/60* | (2022.01) |
| *C05F 17/90* | (2020.01) |
| *C05F 17/921* | (2020.01) |
| *C05F 17/95* | (2020.01) |
| *C05F 17/964* | (2020.01) |
| *C12M 1/00* | (2006.01) |

(Continued)

(52) U.S. Cl.
CPC ............... *B09B 3/70* (2022.01); *B09B 3/60* (2022.01); *C05F 17/90* (2020.01); *C05F 17/921* (2020.01); *C05F 17/95* (2020.01); *C05F 17/964* (2020.01); *C12M 23/36* (2013.01); *C12M 23/58* (2013.01); *C12M 29/20* (2013.01); *C12M 33/20* (2013.01)

(58) Field of Classification Search
CPC .... C05F 17/979; C05F 17/964; C05F 17/971; C05F 17/00
USPC .......................................... 435/290.1–290.4
See application file for complete search history.

(56) References Cited

U.S. PATENT DOCUMENTS

| | | | | |
|---|---|---|---|---|
| 2,035,265 | A | * | 3/1936 | Edwards ................ F02M 61/08 239/453 |
| 2,043,265 | A | | 6/1936 | Roeder |
| 9,040,289 | B2 | | 5/2015 | Mathsen et al. |

(Continued)

FOREIGN PATENT DOCUMENTS

WO 2004022508 A1 3/2004

*Primary Examiner* — Michael L Hobbs
(74) *Attorney, Agent, or Firm* — Boon Intellectual Property Law, PLLC; Brian S. Boon

(57) ABSTRACT

A system and method for vertically-oriented, modular, automated, emissions-controlled composting. In an embodiment, the system and method involve construction of a vertically-oriented set of composting modules comprising a receiving and offloading level, one or more composting bay levels, a feedstock staging level, a biofilter level, a vertical conveyor for uploading feedstock to the feedstock staging level, a freight and personnel elevator, and a leachate tank. This composting system and method reduces the land area required for composting, increases the capture of emissions from composting, and reduces the labor-intensive and heavy-equipment-intensive nature of current methods.

20 Claims, 12 Drawing Sheets

(51) Int. Cl.
 *C12M 1/107* (2006.01)
 *C12M 1/26* (2006.01)

(56) References Cited

U.S. PATENT DOCUMENTS 11,858,016 B1 * 1/2024 West .......................... B09B 3/70
2008/0022739 A1 1/2008 Aswani

* cited by examiner

SYSTEM AND METHOD FOR VERTICALLY-ORIENTED COMPOSTING

CROSS-REFERENCE TO RELATED APPLICATIONS

Priority is claimed in the application data sheet to the following patents or patent applications, each of which is expressly incorporated herein by reference in its entirety:
Ser. No. 18/301,235
63/440,917

BACKGROUND OF THE INVENTION

Field of the Art

The present invention is in the field of waste handling and treatment, and more particularly in the field of composting of organic materials.

Discussion of the State of the Art

Organic waste such as food waste, green waste, and livestock waste is often the largest portion of the waste disposal stream. Rather than simply depositing organic waste into landfills, it can be composted to create a nutrient-rich and organism-rich organic mixture usable for soil conditioning, soil replacement, planting mixtures, fertilizer, carbon sequestration, and plant disease management. Composting thus reduces the amount of waste that goes into landfills thus minimizing generation of greenhouse gases and also creates a useful agricultural product.

There is a large amount of organic waste generated every year. The total generation of municipal solid waste in the U.S. in 2018 was 292.4 million tons, roughly 117 million tons of which (about 40%) was organic waste. Only 42.6 million tons of that organic waste was composted or otherwise managed. The rest ended up in landfills. Composting accounted for only 25 million tons of the 117 million tons of organic waste.

Efforts to expand composting are hampered by the current composting methodologies. Current methods of composting are land-intensive. Compost is created in piles spread out over large lots of land and turned using heavy equipment. This methodology results in a number of substantial restrictions on composting. First, it places a limit on the amount of compost that can be created per unit of land as compost can only be piled to a certain height above which too much heat is generated within the compost pile. Second, since large areas of land are required, composting facilities must be located outside of urban areas where the organic waste is generated, causing increased transportation costs and bottlenecks. Third, such facilities are typically "open air" facilities, meaning that a minimal amount of emissions from the composting process are captured. Even where some emissions are captured through the use of covers over compost piles or via negative aeration, the covers are inefficient at capturing emissions, negative aeration is only utilized during a portion of the composting process both of which negatively impact composting operations. Thus, the failure to capture emissions requires that composting facilities be located away from residential locations even where sufficient land space exists nearby. Fourth, composting operations at such facilities are highly labor intensive, requiring continuous heavy equipment operations to move materials through each phase of the process.

What is needed is a system and method for composting which reduces the land area required for composting, increases the capture of emissions from composting, and reduces the labor-intensive and heavy-equipment-intensive nature of current methods.

SUMMARY OF THE INVENTION

Accordingly, the inventor has conceived and reduced to practice, a system and method for vertically-oriented, modular, automated, emissions-controlled composting. In an embodiment, the system and method involve construction of a vertically-oriented set of composting modules comprising a receiving and offloading level, one or more composting bay levels, a feedstock staging level, a biofilter level, a vertical conveyor for uploading feedstock to the feedstock staging level, a freight and personnel elevator, and a leachate tank. This composting system and method reduces the land area required for composting, significantly increases the capture of emissions from composting, and reduces the labor-intensive and heavy-equipment-intensive nature of current methods.

According to a preferred embodiment, a vertically-oriented composting facility is disclosed, comprising: a receiving and offloading level configured to receive feedstock for composting and allow for offloading of compost; one or more composting bay levels, each composting bay level comprising: one or more composting bins, each composting bin comprising: a bin loading area at a first end of the composting bin, configured to receive the feedstock via gravity from a transition chute located above the bin loading area; a transition chute opening at a second end of the composting bin into which feedstock may be dropped; a horizontal conveyor comprising an aerated floor and configured to convey the feedstock from the bin loading area to the transition chute opening; an aeration system comprising a high volume fan providing air flow under pressure to the feedstock through the aerated floor aerated floor of the horizontal conveyor; a leachate collection system comprising piping configured to collect leachate from the feedstock which drains through the aerated floor of the horizontal conveyor; and an emissions collection system comprising: a second air pump configured to draw air from the bin and transfer it for emissions filtering; and a non-permeable cover or enclosure around the bin having an opening at either the first or second end of the bin and a connection to the second air pump at the other end, such that air within the enclosure is drawn across the bin from the opening to the second air pump.

According to an aspect of an embodiment, the composting facility is constructed as a single structure.

According to an aspect of an embodiment, one or more of the levels is a modular construction which can be stacked on top of other levels of the composting facility.

According to an aspect of an embodiment, the composting facility is constructed as a hybrid structure comprising a single structure constructed on a ground surface, with one or more levels being modular construction stacked on top of the single structure or on top of other modular levels.

According to an aspect of an embodiment, each of the one or more composting bay levels has a plurality of composting bins.

According to an aspect of an embodiment, the horizontal conveyor is a moving floor.

According to an aspect of an embodiment, aeration of the feedstock is provided by a dual-purpose aeration and leachate system comprising piping attached to one or more slats of the moving floor, the piping having risers extending up toward holes in the surface of the moving floor configured to both provide pressured air to the feedstock and receive leachate, wherein the aeration is provided by the first air pump connected to the piping via a flexible hose, and leachate drainage from the piping is provided by a flexible hose connected to a lower portion of the piping.

According to an aspect of an embodiment, the horizontal conveyor is a porous belt or track.

According to an aspect of an embodiment, aeration of the feedstock is provided by a dual-purpose aeration and leachate system comprising a collection pan or tray with a cover having holes for aeration and piping from the collection pan or tray, wherein the porous belt or track slides over the top of the cover and wherein holes, slits, or gaps in the conveyor belt or track periodically coincide with the holes in the cover, wherein the aeration is provided by the first air pump connected to the collection pan or tray and leachate is collected in the collection pan or tray and leachate drainage is provided by piping connected to a lower portion of the collection pan or tray.

According to an aspect of an embodiment, turning of the feedstock is performed by dropping of the feedstock through the transition chute opening to a lower level of the composting facility.

According to an aspect of an embodiment, the feedstock is dropped by movement of the feedstock toward the transition chute opening by the horizontal conveyor.

According to an aspect of an embodiment, the feedstock is dropped via the transition chute opening onto a bin loading area of a composting bin of the lower level.

According to an aspect of an embodiment, moisturization, or inoculation, or both are performed by sprayers as the feedstock drops to the lower level of the composting facility.

BRIEF DESCRIPTION OF THE DRAWING FIGURES

DETAILED DESCRIPTION OF THE DRAWING FIGURES

Figure 1:
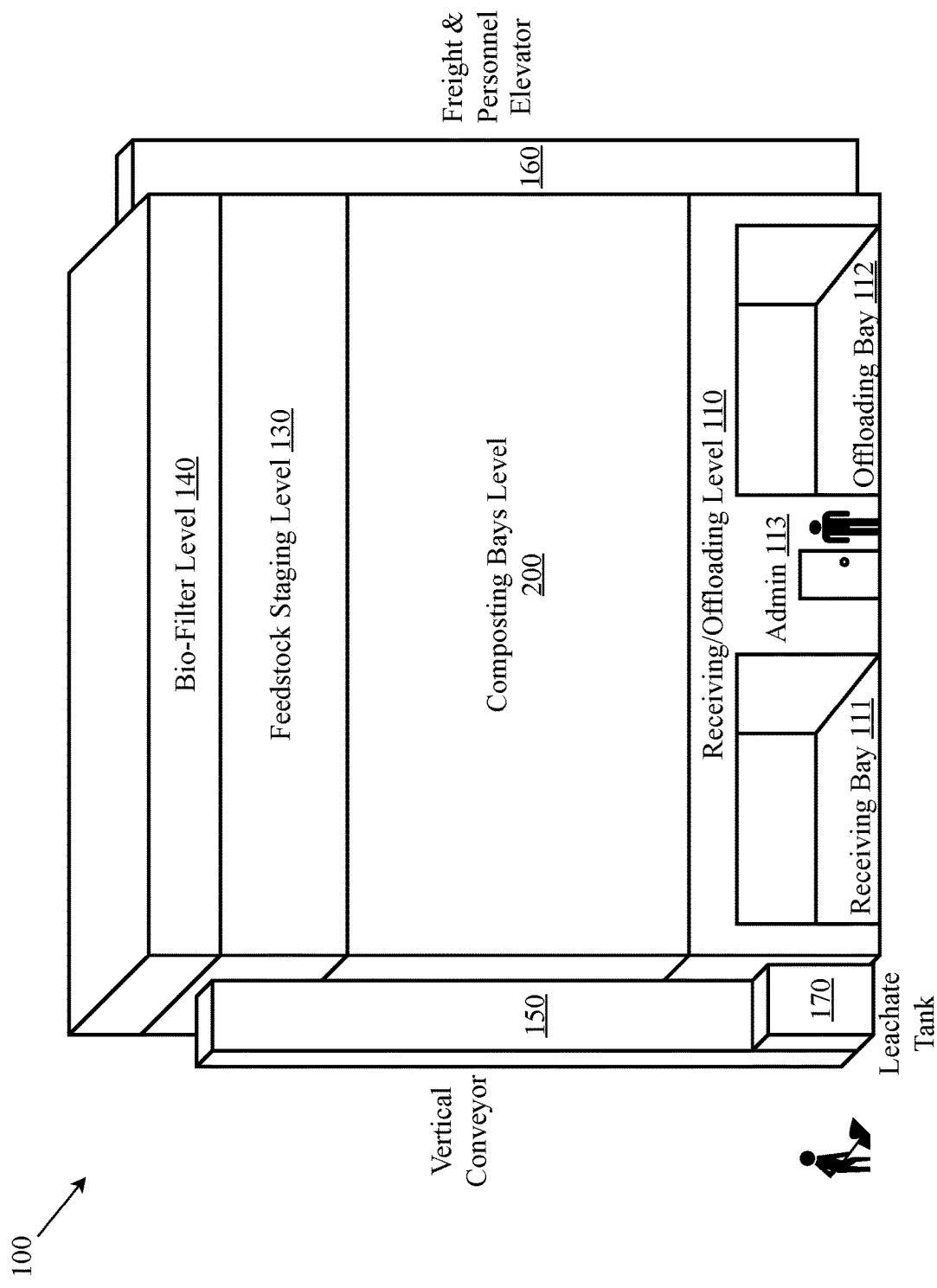
FIG. 1 is a diagram illustrating an exemplary vertically-oriented, modular composting facility.

The inventor has conceived, and reduced to practice, a system and method for vertically-oriented, modular, automated, emissions-controlled composting. In an embodiment, the system and method involve construction of a vertically-oriented set of composting modules comprising a receiving and offloading level, one or more composting bay levels, a feedstock staging level, a biofilter level, a vertical conveyor for uploading feedstock to the feedstock staging level, a freight and personnel elevator, and a leachate tank. This composting system and method reduces the land area required for composting, increases the capture of emissions from composting, and reduces the labor-intensive and heavy-equipment-intensive nature of current methods.

Efforts to expand composting are hampered by the current composting methodologies. Current methods of composting are land-intensive. Compost is created in piles spread out over large lots of land and turned using bulldozers and other heavy equipment. This methodology results in a number of substantial restrictions on composting. First, it places a limit on the amount of compost that can be created per unit of land as compost can only be piled to a certain height above which too much heat is generated within the compost pile. Second, since large areas of land are required, composting facilities must be located outside of urban areas where the organic waste is generated, causing increased transportation costs and bottlenecks. Third, such facilities are typically "open air" facilities, meaning that little or no emissions from the composting process are captured. Even where some emissions are captured through the use of covers over compost piles, the covers are inefficient at capturing emissions, and substantially hamper composting operations. Thus, the failure to capture emissions requires that composting facilities be located away from residential locations even where sufficient land space exists nearby. Existing composting facilities do not even attempt to quantify or document their emissions, so emissions from such facilities are largely unknown at this time. Fourth, composting operations at such facilities are highly labor intensive, requiring continuous heavy equipment operations to turn compost piles.

The composting system and method herein described remedy these deficiencies by reducing the land area required for composting, increasing the capture of emissions from composting, and reducing the labor-intensive and heavy-equipment-intensive nature of current methods. The system comprises a vertical composting structure having different levels for different operations. The system may be constructed as a single, stand-alone structure, or as a set of separately-constructed modules that can be stacked on top of one another to form the composting system, or some combination of both (i.e., some portions of the composting system could be constructed as a permanent structure while others could be modules such as composting bins that can be added or removed from the structure to, for example, increase or decrease processing capacity). Regarding emissions, specifically, the composting system and method herein described allow for real time sampling of air emissions to quantify, document, and adjust emissions from the composting process.

In an embodiment, the system and method involve construction of a vertically-oriented set of composting modules comprising a receiving and offloading level, one or more composting bay levels, a feedstock staging level, a biofilter level, a vertical conveyor for uploading feedstock to the feedstock staging level, a freight and personnel elevator, and a leachate tank. This composting system and method reduces the land area required for composting, increases the capture of emissions from composting, and reduces the labor-intensive and heavy-equipment-intensive nature of current methods. The composting bays level may comprise multiple bay levels, wherein compost is turned not by heavy equipment operations, but rather by dropping the compost from a higher bay level to a lower one. Each bay level comprises one or more composting bins, each of which is fitted with a horizontal conveyor such as a "moving floor" (such as the Walking Floor®) which conveys the compost material from bin loading area (from the bay above) to the transition chute to the next bay level down. The horizontal conveyor has an aerated floor fitted with holes, slits, or sections which serve the dual purposes of aeration and leachate collection. Each composting bin is further fitted with a cover such as a flexible hoop bay cover and a vacuum system whereby emissions are drawn from bin loading area end to the transition chute end and out to a biofilter prior to venting to the environment.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

DETAILED DESCRIPTIONS OF THE DRAWING FIGURES

FIG. 1 is a diagram illustrating an exemplary vertically-oriented, modular composting facility 100. Composting facility 100 as herein described reduces the land area required for composting, increases the capture of emissions from composting, and reduces the labor-intensive and heavy-equipment-intensive nature of current methods. The system comprises a vertical composting structure having different levels for different operations. The system may be constructed as a single, stand-alone structure, or as a set of separately-constructed modules that can be stacked on top of one another to form the composting system, or some combination of both (i.e., some portions of the composting system could be constructed as a permanent structure while others could be modules such as composting bins that can be added or removed from the structure to, for example, increase or decrease processing capacity).

In this exemplary embodiment, the composting facility is a vertically-oriented set of composting modules comprising a receiving and offloading level 110, a composting bay level 200 comprising one or more composting bays, a feedstock staging level 130, a biofilter level 140, a vertical conveyor 150 for uploading feedstock to the feedstock staging level, a freight and personnel elevator 160, and a leachate tank 170.

Receiving and offloading level 110 is the bottom level of the structure and is typically built at ground level so that composting feedstock and finished compost can be loaded and unloaded using heavy equipment such as front loaders. Receiving and offloading level 110 comprises a receiving bay 111, an offloading bay 112, and optionally administrative facilities 113 such as offices, control rooms, and crew rooms. Receiving bay 111 receives compost feedstock for processing into compost, and may comprising equipment for grinding and blending the feedstock prior to transfer up the vertical conveyor to a feedstock staging area to start the composting process. Offloading bay 112 receives finished compost from composting bay level 200, and may comprising equipment for screening of finished compost and loading of finished compost onto outbound transportation (e.g., trucks, trains, etc.) or onto conveyors to nearby storage facilities. Administrative facilities 113 for composting facility 100 such as offices, control rooms, and crew rooms are conveniently located at receiving and offloading level 110.

Composting bay level 200 comprises one or more composting bays arranged vertically, wherein compost is turned not by heavy equipment operations, but rather by dropping the compost from a higher bay level to a lower one. Each bay level comprises one or more composting bins, each of which is fitted with a horizontal conveyor such as a "moving floor" which conveys the compost material from bin loading area (from the bay above) to the transition chute to the next bay level down. The horizontal conveyor has an aerated floor fitted with holes, slits, or sections which serve the dual purposes of aeration and leachate collection. Each composting bin is further fitted with a cover such as a flexible hoop bay cover and a vacuum system whereby emissions are drawn from bin loading area end to the transition chute end and out to a biofilter prior to venting to the environment. Note that while a moving floor is a convenient conveyor, other forms of conveyance may also be used including, but not limited to, a single-piece flexible conveyor belt with holes or slits for aeration and leachate collection underneath the belt, a multiple-piece conveyor belt (having either longitudinal strips along the length of the bin or transverse strips across the width of the bin) with aeration and leachate collection between the pieces of the belt, and a conveyor track configured similarly to a conveyor belt but having hard slats mechanically connected to one another with aeration and leachate collection between the pieces of the track. In some configurations, a solid floor may be used instead of a conveyor, the solid floor having holes or slits for aeration and leachate collection and the feedstock being moved by small equipment such as frontend loaders or bulldozers.

Feedstock staging level 130 receives feedstock from vertical conveyor 150 into a feedstock staging area. Feedstock may be fed from feedstock staging area via horizontal conveyors such as moving floors, or via small equipment such as frontend loaders and bulldozers. At the feedstock staging area, feedstock can be inoculated with microorganisms beneficial to the composting process and moisturized to optimal levels for composting. Feedstock staging area may be further fitted with dust control to remove potentially harmful dust from dry feedstock materials such as wood chips.

Biofilter level 140 will typically be at the top of composting facility 100. One or more biofilters at biofilter level 140 will receive emissions from emissions collection systems in the composting bins at composting bays level 200, and force the emissions up through a biofilter material comprising organic material which supports a population of microorganisms which oxidize biodegradable gasses into carbon dioxide, water, and mineral salts. The biofilter material may comprise peat, soil, compost, wood chips, straw, or other material and mixtures which provide a suitable environment for microbial growth and maintain a high porosity to allow air to flow easily. Important considerations in biofilter material selection are the type of biofilter material, the thickness of the biofilter material layer, airflow through the biofilter material layer, nutrient content, and moisture control. Properly designed biofilters will remove the majority of odor-causing agents from compost emissions, allowing for venting of filtered emissions to the outside environment.

Vertical conveyor 150 transfers feedstock from receiving and offloading level 110 to feedstock staging level 130. A variety of types of vertical conveyors exist and may be used. The most suitable types of vertical conveyor for this application would be either a vertical screw-type conveyor which pushes feedstock upward along the threads of a large, vertically-mounted, rotating screw, or a vertical belt-type conveyor which carries feedstock up a vertically-mounted belt on which buckets are mounted for carrying the feedstock.

The freight and personnel elevator 160 is a typical industrial freight elevator configured to carry people and/or equipment to the various levels of composting facility 100 for operation and maintenance of the facility.

Leachate tank 170 is a liquid storage tank configured for capture and storage of leachate for later treatment or disposal. Compost leachate is liquid that drains from feedstock during composting. Leachate contains soluble minerals, organic matter, and suspended solids, including mineral and organic colloids. The exact composition of the leachate is determined by the nature of the feedstock, the degree of progress of the composting process, and the composition of any liquid that infiltrates into the compost. If feedstock contains any contaminants such as metals or hydrocarbons, leachate will likely contain those, as well. Leachate is typically collected in tanks or pools for treatment or disposal. Leachate tank 170 is shown here as being above ground and outside the main structure, but may be located in other places such as underground or inside the main structure.

Figure 2:
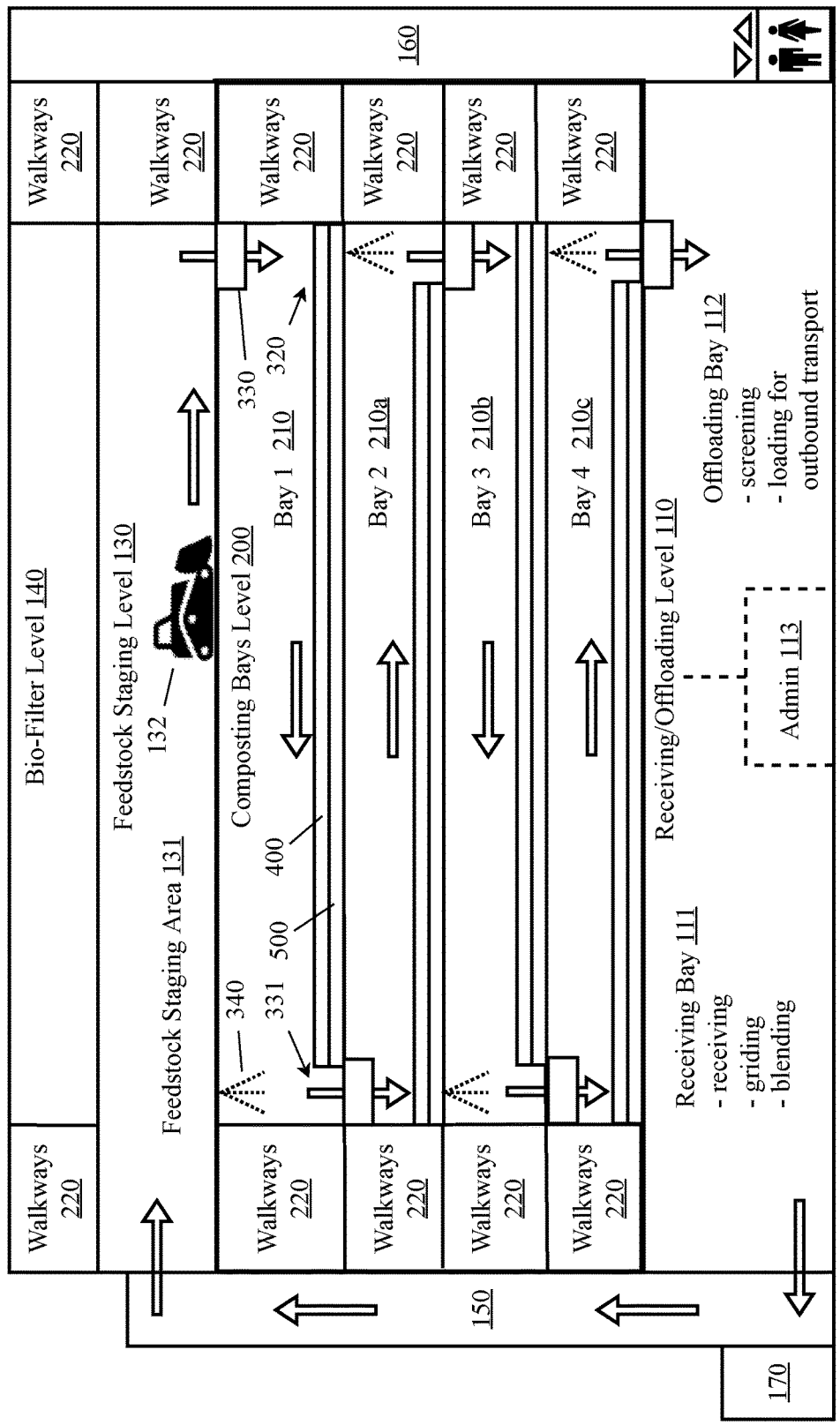
FIG. 2 is a cross-sectional diagram illustrating an exemplary interior organization of a vertically-oriented, modular composting facility.

FIG. 2 is a cross-sectional diagram illustrating an exemplary interior organization of a vertically-oriented, modular composting facility. Composting facility 100 as herein described reduces the land area required for composting, increases the capture of emissions from composting, and reduces the labor-intensive and heavy-equipment-intensive nature of current methods. The system comprises a vertical composting structure having different levels for different operations. The system may be constructed as a single, stand-alone structure, or as a set of separately-constructed modules that can be stacked on top of one another to form the composting system, or some combination of both (i.e., some portions of the composting system could be constructed as a permanent structure while others could be modules such as composting bins that can be added or removed from the structure to, for example, increase or decrease processing capacity).

In this exemplary embodiment, the composting facility is a vertically-oriented set of composting modules comprising a receiving and offloading level 110, a composting bay level 200 comprising one or more composting bays, a feedstock staging level 130, a biofilter level 140, a vertical conveyor 150 for uploading feedstock to the feedstock staging level, a freight and personnel elevator 160, and a leachate tank 170. Each level of composting facility may be configured with personnel walkways 220 for personnel to manage the operations of composting facility 100 at each level.

Receiving and offloading level 110 is the bottom level of the structure and is typically built at ground level so that composting feedstock and finished compost can be loaded and unloaded using heavy equipment such as front loaders. Receiving and offloading level 110 comprises a receiving bay 111, an offloading bay 112, and optionally administrative facilities 113 such as offices, control rooms, and crew rooms. Receiving bay 111 receives compost feedstock for processing into compost, and may comprising equipment for grinding and blending the feedstock prior to transfer up the vertical conveyor to a feedstock staging area to start the composting process. Offloading bay 112 receives finished compost from composting bay level 200, and may comprising equipment for screening of finished compost and loading of finished compost onto outbound transportation (e.g., trucks, trains, etc.) or onto conveyors to nearby storage facilities. Administrative facilities 113 for composting facility 100 such as offices, control rooms, and crew rooms are conveniently located at receiving and offloading level 110.

Composting bay level 200 comprises one or more composting bays 210, 210*a-c* arranged vertically, wherein compost is turned not by heavy equipment operations, but rather by dropping the compost from a higher bay level to a lower one. Here, Bay 1 210 is shown and described, and Bays 2-3 210*a-c* are similarly configured. Composting bays level 200 may comprise any number of such bays 210, 210*a-c*. Each bay level 210 comprises one or more composting bins, each of which is fitted with a horizontal conveyor 400 which conveys the compost material from bin loading area 320 (from the bay above via a transition chute 330) to a transition chute opening 331 to the next bay level down. Turning of compost feedstock is accomplished via the vertical drop of the feedstock from a higher bay level to a lower one via transition chute 330. Inoculation and moisturizing of feedstock may be performed at turning via sprayers 340. Horizontal conveyor 400 has an aerated floor fitted with holes, slits, or sections which serve the dual purposes of aeration and leachate collection via an aeration and leachate collection system 500. Each bay level comprises one or more composting bins, each of which is fitted with a horizontal conveyor such as a "moving" or "live" floor (an example of which is a Walking Floor®) which conveys the compost material from bin loading area (from the bay above) to the transition chute to the next bay level down. Each composting bin is further fitted with an impermeable cover or enclosure (not shown) such as a flexible hoop bay cover and a vacuum system (not shown) whereby emissions are drawn from bin loading area 320 end to transition chute 330 end and out to biofilter level 140 prior to venting to the environment.

Feedstock staging level 130 receives feedstock from vertical conveyor 150 into a feedstock staging area. Feedstock may be fed from feedstock staging area via a horizontal conveyor such as moving floors, or via small equipment such as frontend loaders and bulldozers. At the feedstock staging area, feedstock can be inoculated with microorganisms beneficial to the composting process and moisturized to optimal levels for composting. Feedstock staging area may be further fitted with dust control to remove potentially harmful dust from dry feedstock materials such as wood chips.

Biofilter level 140 will typically be at the top of composting facility 100 but can be located elsewhere depending on the facility design. One or more biofilters at biofilter level 140 will receive emissions from emissions collection systems in the composting bins at composting bays level 200, and force the emissions up through a biofilter material comprising organic material which supports a population of microorganisms which oxidize biodegradable gasses into carbon dioxide, water, and mineral salts. The biofilter material may comprise peat, compost, wood chips, Bio-char, or other material and mixtures which provide a suitable environment for microbial growth and maintain a high porosity to allow air to flow easily. Important considerations in biofilter material selection are the type of biofilter material, the thickness of the biofilter material layer, airflow through the biofilter material layer, nutrient content, and moisture control. Properly designed biofilters will remove the majority of odor-causing agents from compost emissions, allowing for venting of filtered emissions to the outside environment.

Vertical conveyor 150 transfers feedstock from receiving and offloading level 110 to feedstock staging level 130. A variety of types of vertical conveyors exist and may be used. The most suitable types of vertical conveyor for this application would be either a vertical screw-type conveyor which pushes feedstock upward along the threads of a large, vertically-mounted, rotating screw, or a vertical belt-type conveyor which carries feedstock up a vertically-mounted belt on which buckets are mounted for carrying the feedstock.

The freight and personnel elevator 160 is a typical industrial freight elevator configured to carry people and/or equipment to the various levels of composting facility 100 for operation and maintenance of the facility.

Leachate tank 170 is a liquid storage tank configured for capture and storage of leachate for later treatment or disposal. Compost leachate is liquid that drains from feedstock during composting. Leachate contains soluble minerals, organic matter, and suspended solids, including mineral and organic colloids. The exact composition of the leachate is determined by the nature of the feedstock, the degree of progress of the composting process, and the composition of any liquid that infiltrates into the compost. If feedstock contains any contaminants such as metals or hydrocarbons, leachate will likely contain those, as well. Leachate is typically collected in tanks or pools for treatment or disposal. Leachate tank 170 is shown here as being above ground and outside the main structure, but may be located in other places such as underground or inside the main structure.

Figure 3:
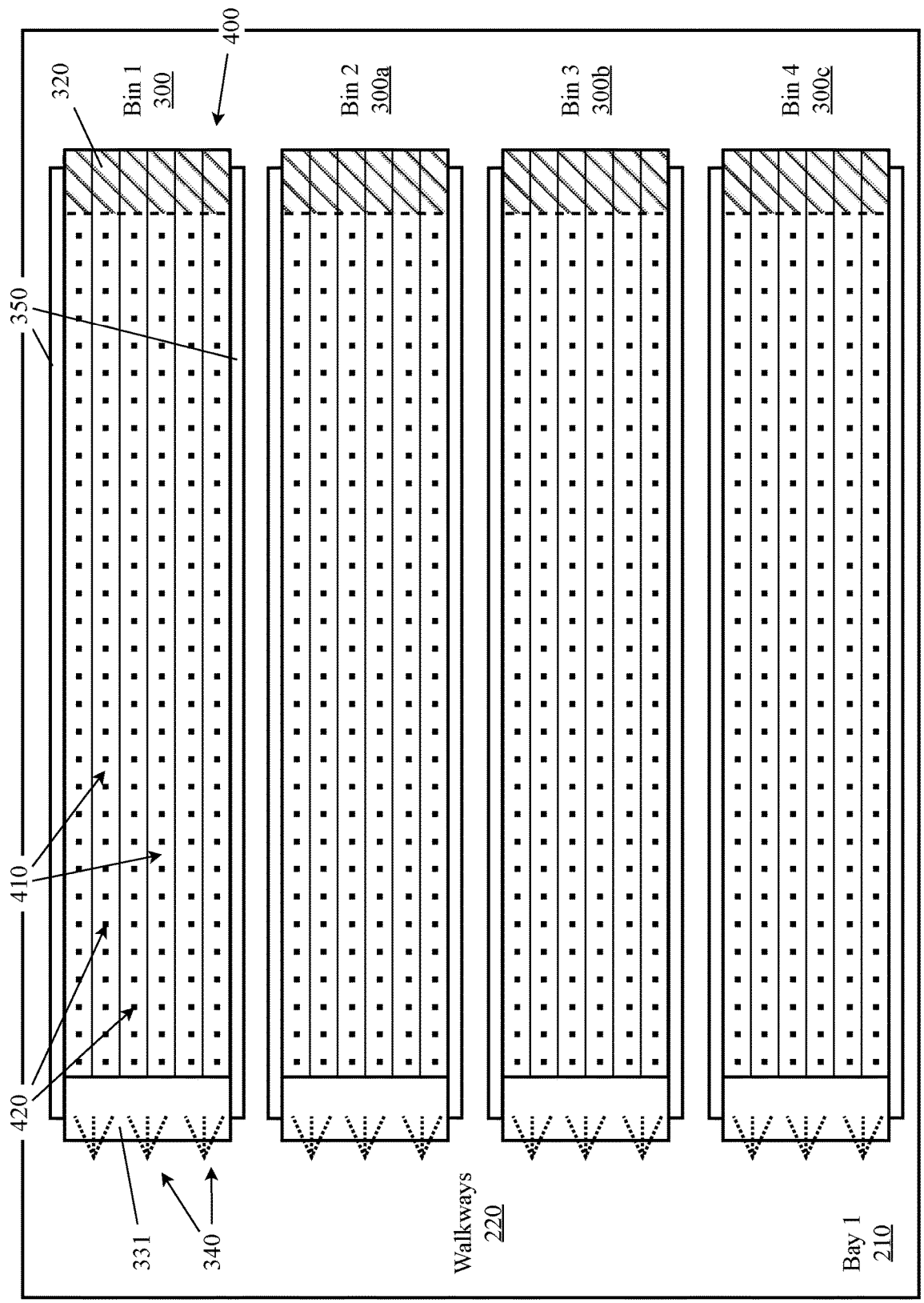
FIG. 3 is a top down diagram illustrating an exemplary modular composting bay of a vertically-oriented, modular composting facility.

FIG. 3 is a top down diagram illustrating an exemplary modular composting bay of a vertically-oriented, modular composting facility. In this exemplary diagram, Bay 1 210 is shown and described, with other bay levels 210*a-c* being similarly configured. Bay 210 comprises one or more composting bins 300, 300*a-c*. Bin 1 300 is shown and described with other bins 300*a-c* being similarly configured. In this example, four composting bins 300, 300*a-c* are shown, but there may be any number of bins 300, 300*a-c* per bay level 210, 210*a-c*, and any number of bay levels in composting facility 100. Thus, in the exemplary configuration of composting facility 100 herein described, there are four bay levels each with four compost bins, for a total of 16 compost bins, but any number of such levels and bins may be used.

Composting bin 300 comprises bin loading area 320, transition chute 330 (not shown) from previous level, transition chute opening 331 to next bay level down, sprayers 340, walls 350, horizontal conveyor 400, and aeration and leachate collection system 500. Compost is received at bin loading area 320 via transition chute 330 (not shown) and is contained via bin walls 350. Horizontal conveyor 400 conveys compost material from bin loading area 320 to a transition chute opening 331 to the next bay level down. Turning of compost feedstock is accomplished via the vertical drop of the feedstock from a higher bay level to a lower one via transition chute where it is agitated and de-clumped 330. Inoculation and moisturizing of feedstock may be performed at turning via sprayers 340. In this diagram, horizontal conveyor 400 is shown with an aerated floor fitted with holes 420 which serve the dual purposes of aeration and leachate collection via an aeration and leachate collection system 500. Each composting bin is further fitted with an impermeable cover or enclosure (not shown) such as a flexible hoop bay cover and a vacuum system (not shown) whereby emissions are drawn from bin loading area 320 end to transition chute 330 end and out to biofilter level 140 prior to venting to the environment.

Figure 4:
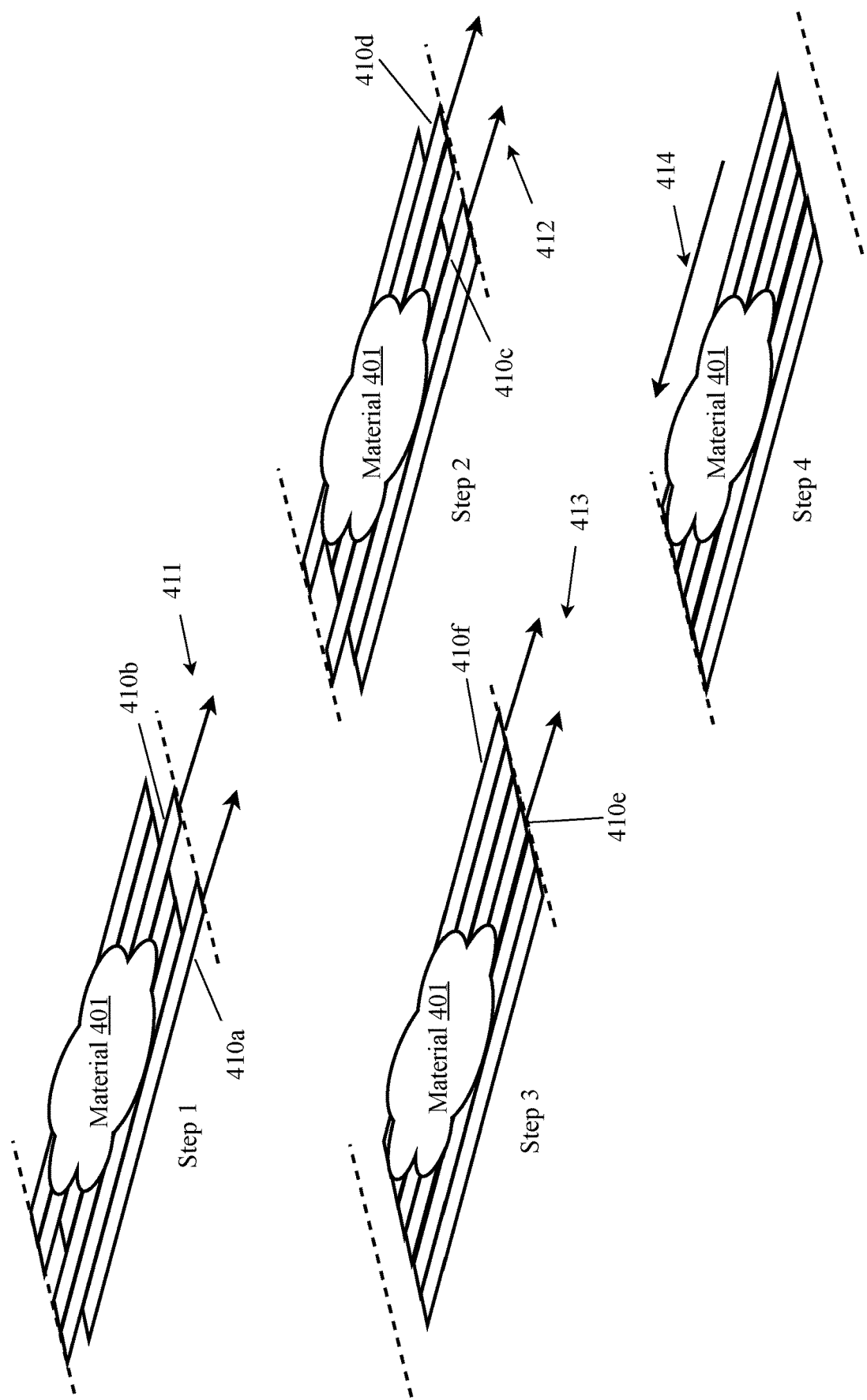
FIG. 4 (PRIOR ART) is a diagram illustrating operation of a moving floor.

FIG. 4 (PRIOR ART) is a diagram illustrating operation of a moving floor. A moving floor is a type of horizontal conveyor for moving material in a desired direction. A moving floor comprises a series of slats 410a-f which alternately draw backward under the material 401 until all slats 410a-f have been drawn backward, at which point all slats 410a-f are pushed forward in unison, carrying the material forward in the desired direction. In a typical configuration, every third slat is drawn backward until all such slats have been drawn backward, but any such configuration may be used (e.g., every second slat, every fourth slat, etc.).

In a first step, slats 410a, b are drawn backward in the direction of arrows 411 underneath material 401. In a second step, slats 410c, d are drawn backward in the direction of arrows 412 underneath material 401. In a third step, slats 410e, f are drawn backward in the direction of arrows 413 underneath material 401. In a fourth and final step, all six slats 410a-f are pushed forward in the direction of arrows 414, carrying the material along with them in the desired direction.

Figure 5:
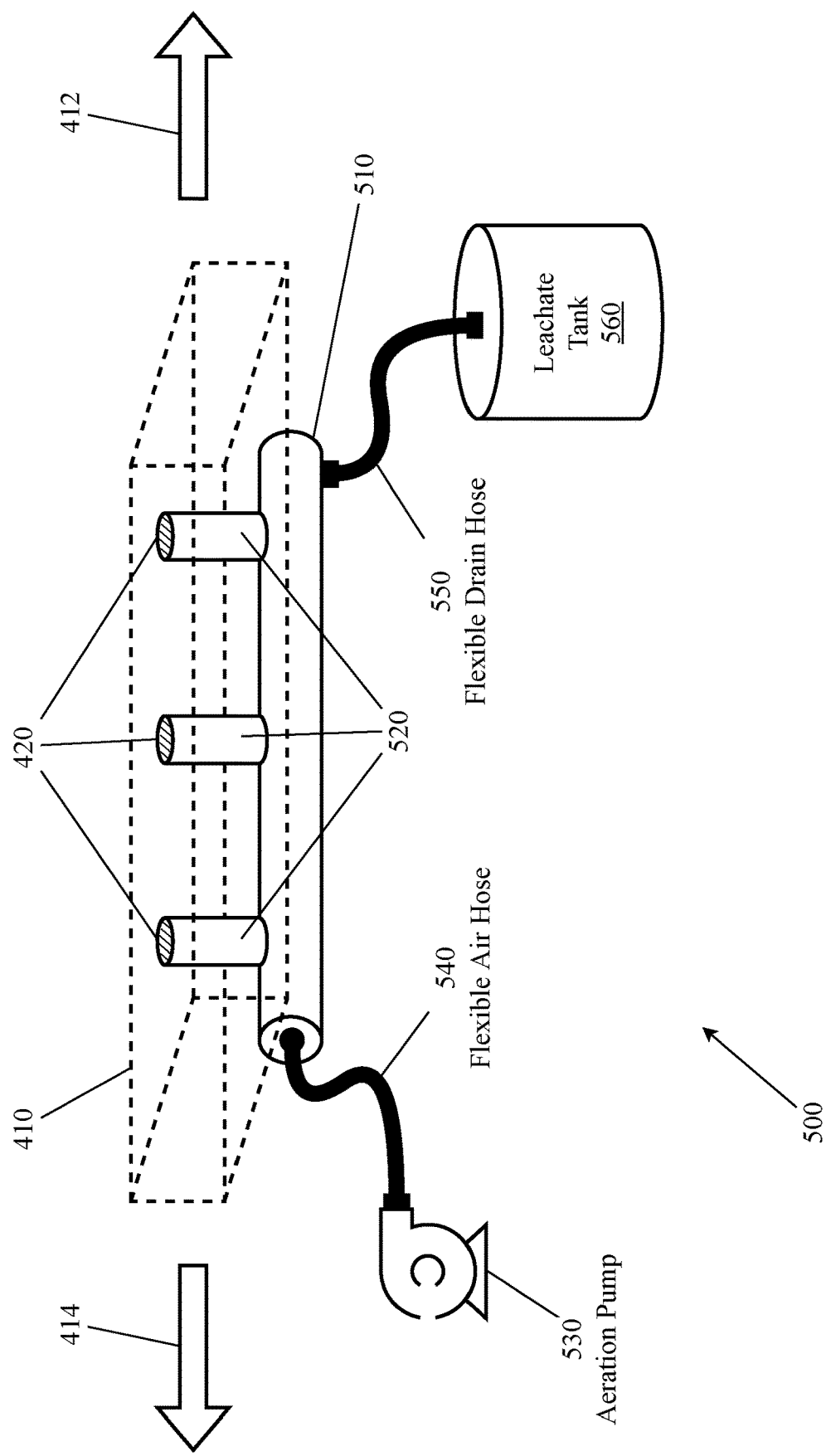
FIG. 5 is a diagram illustrating an exemplary aeration and leachate collection system of a vertically-oriented, modular composting facility.

FIG. 5 is a diagram illustrating an exemplary aeration and leachate collection system of a vertically-oriented, modular composting facility. This exemplary aeration and leachate collection system is configured for use with a walking-floor-type horizontal conveyor system. In this exemplary embodiment, a pipe 510 is physically attached to a slat 410 of a moving floor. Pipe 510 has risers 420 extending up from pipe 510 through slat 410 ending in open holes 420 flush with or lower than holes in slat 410. An air pump 530 (e.g., a fan, blower, pump, bellows, or other device configured to move air) forces air at an appropriate rate (determined by the stage of composting, porosity of feedstock, and other factors) via a flexible air hose 540 into pipe or tube 510, up through risers 520, and out of holes 420 into feedstock. At the same time, leachate flows from feedstock into holes 420, down risers 520, into pipe 510, and out of a flexible drain hose 550 connected to the bottom of pipe 510, and into leachate tank 560. Both aeration and leachate collection can occur simultaneously through the same holes 420 and risers 520 as the flow volume of leachate will rarely be sufficient to fully occlude risers and even where flow volume is high, leachate will manage to drip or seep downward into risers despite air flow in the opposite direction. As slat 410 moves backward (arrow 414) and forward (arrow 412) in its operation as part of a moving floor, flexible hoses 540, 550 allow for movement of slat 410, pipe 510, and risers 520. In some embodiments, pipe 510 or slat 410 may be placed on a slope toward leachate tank 560 to facilitate drainage of leachate from pipe 510.

This exemplary aeration and leachate collection system is shown in the context of a moving floor, but can be applied to any sort of horizontal conveyor. In embodiments where other horizontal conveyors are used (e.g., a conveyor belt, a conveyor track, etc.), the aeration and leachate collection system may be configured as a collection pan or tray with a cover having holes for aeration and piping from the collection pan or tray, wherein the belt or track slides over the top of the cover and wherein holes, slits, or gaps in the conveyor belt or track periodically coincide with the holes in the cover and leachate is collected in the pan or tray and routed leachate tank via piping.

Figure 6:
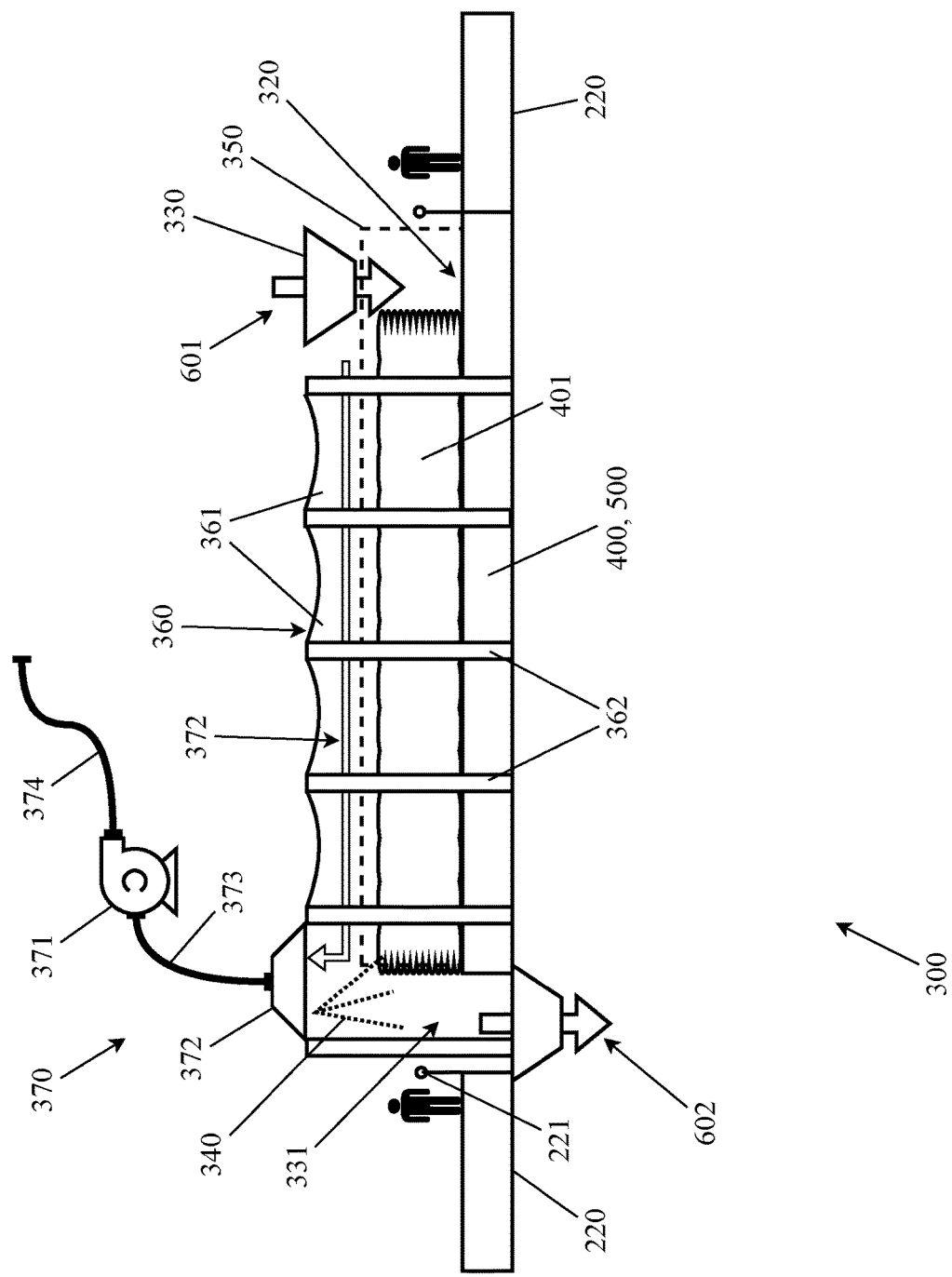
FIG. 6 is a side view diagram illustrating an exemplary composting bin of a vertically-oriented, modular composting facility.

FIG. 6 is a side view diagram illustrating an exemplary composting bin of a vertically-oriented, modular composting facility. Bin 300 is fitted with a horizontal conveyor 400 which conveys the compost material (i.e., feedstock) 401 from bin loading area 320 (from the bay above via a transition chute 330 as indicated by arrow 601) to a transition chute opening 331 to the next bay level down (as indicated by arrow 602). Turning of compost feedstock is accomplished via the vertical drop of the feedstock from a higher bay level to a lower one via transition chute 330. Inoculation and moisturizing of feedstock may be performed at turning via sprayers 340. Horizontal conveyor with aeration and leachate system 400, 500 is as described above. Horizontal conveyor 400 has an aerated floor fitted with holes, slits, or sections which serve the dual purposes of aeration and leachate collection via an aeration and leachate collection system 500. Bin 300 is fitted with walls 350 (transparent in this diagram to show compost material contained between them) to contain compost material 401 as it proceeds along bin, and a horizontal conveyor 400 such as a "moving floor" which conveys the compost material from bin loading area (from the bay above) to the transition chute to the next bay level down. Bin 300 is further fitted with an impermeable cover or enclosure. In this exemplary diagram, the impermeable cover or enclosure is a flexible hoop bay cover 360 comprising an impermeable material 361 such as a plastic sheet held up by hoop supports 362 such that flexible hoop bay cover 360 encloses all or part of the compost material 401 with an opening at bin loading area 320 end of bay 300. A vacuum system 370 comprises an air pump 371 (e.g., a fan, blower, pump, bellows, or other device configured to move air), a hood 372 connected to the cover or enclosure, a hose or piping 373 from the hood to the pump, and a hose or piping 374 to the biofilter level 140. Vacuum system 370 draws air from the opening at bin loading area 320 through flexible hoop bay cover 360 in the direction of arrow 372, into vacuum system comprising a hood 370 and hose 371, and to biofilter level 140, thus capturing emissions from the composting process and filtering them before venting to the environment. Also, shown for clarity are personnel walkways 220 and railings 221.

Figure 7:
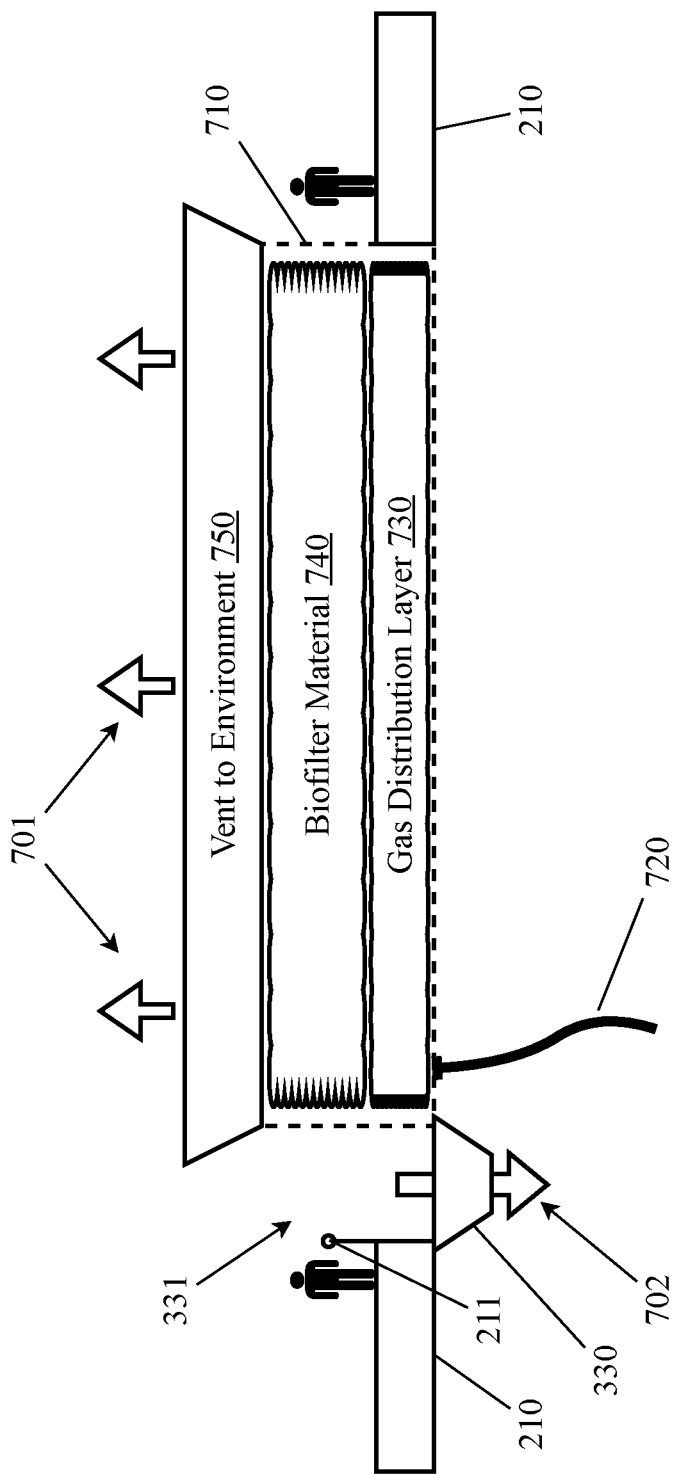
FIG. 7 is a side view diagram illustrating a biofilter module of a vertically-oriented, modular composting facility.

FIG. 7 is a side view diagram illustrating a biofilter module of a vertically-oriented, modular composting facility. Biofilter level 140 will typically be at the top of composting facility 100. One or more biofilters 710 at biofilter level 140 will receive emissions from emissions collection systems in the composting bins at composting bays level 200 via a hose 720 or other suitable piping, and force the emissions up through a biofilter material 740 comprising organic material which supports a population of microorganisms which oxidize biodegradable gasses into carbon dioxide, water, and mineral salts. Biofilter 710 further comprise a gas distribution layer 730 such as a layer of gravel through which the emissions may evenly disperse for consistent distribution throughout biofilter material 740 or a horizontal conveyor 400 such as the moving floor embodiments described herein. Biofilter material 740 may comprise peat, soil, compost, wood chips, straw, or other material and mixtures which provide a suitable environment for microbial growth and maintain a high porosity to allow air to flow easily. Important considerations in biofilter material 740 selection are the type of biofilter material, the thickness of the biofilter material layer, airflow through the biofilter material layer, nutrient content, and moisture control. Properly designed biofilters will remove the majority of odor-causing agents from compost emissions, allowing for venting of filtered emissions to the outside environment via a vent to the environment 750 in the direction of arrows 701. Also, shown for clarity are personnel walkways 220 and railings 221.

While a single biofilter is shown in this diagram for the sake of clarity and simplicity, a plurality of such biofilters may be used either in parallel, in series, or in a recirculating configuration where already-filtered emissions are re-circulated through one or more biofilters to achieve higher levels of emissions control. In this exemplary configuration, biofilter layer 140 further comprises a transition chute opening 331 which may be used either to dispose of biofilter material 740 when saturated with or decomposed, or in some cases to incorporate biofilter material 740 into feedstock for composting bins at composting bays level 200, both via transition chute 330 as indicated by arrow 702. Where a horizontal conveyor 400 is used as gas distribution layer 730, biofilter material 740 is easily transferred to transition chute opening 331 as described herein above.

Figure 8:
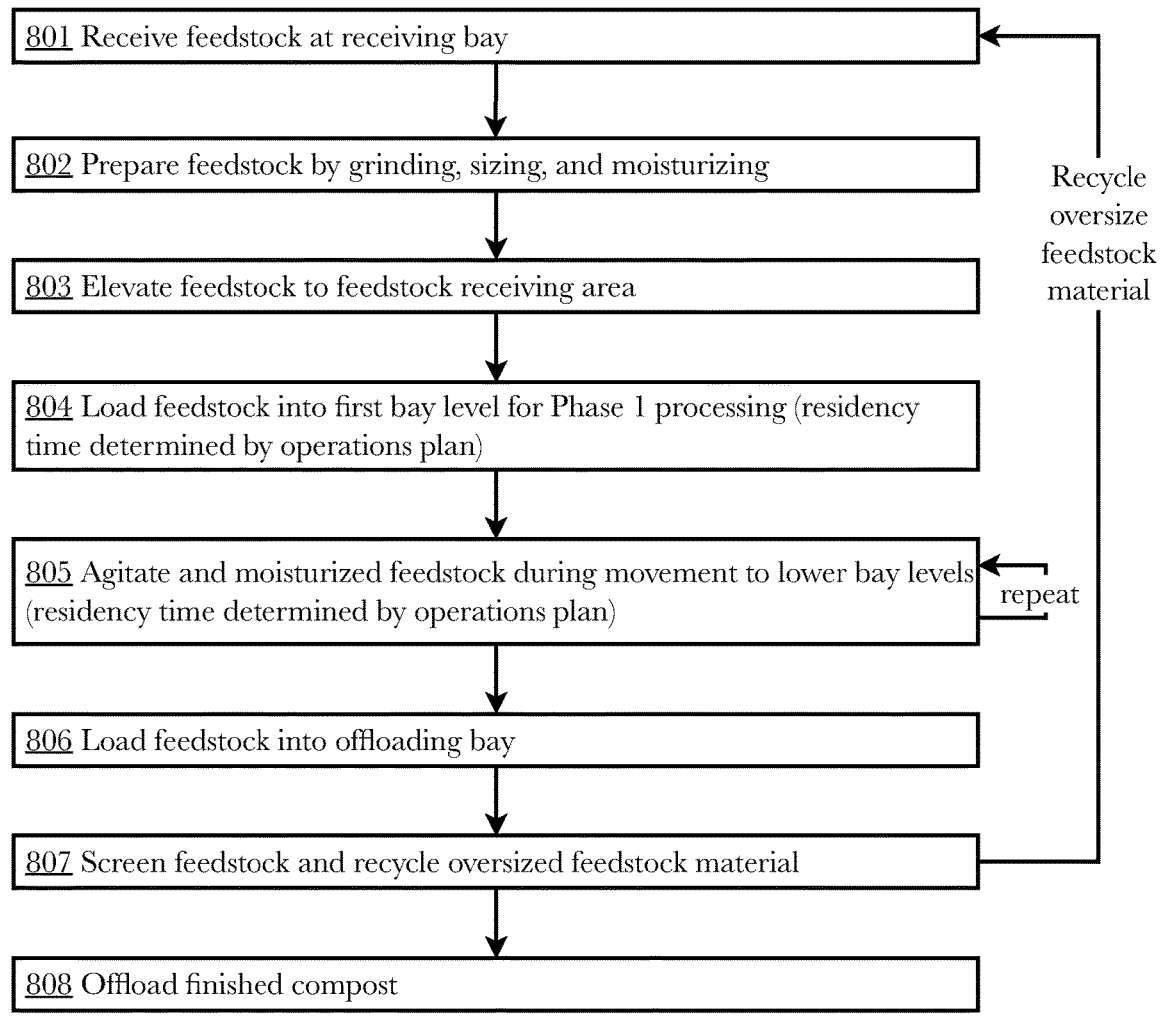
FIG. 8 is a flow diagram illustrating an exemplary overall composting process for a vertically-oriented, modular composting facility.

FIG. 8 is a flow diagram illustrating an exemplary overall composting process for a vertically-oriented, modular composting facility. At step 801, feedstock is received at receiving bay 111. At step 802, the feedstock is prepared by grinding it, filtering or sorting it by size, and moisturizing it. At step 803, the feedstock is elevated via vertical conveyor 150 to feedstock staging area 131. At step 804, the feedstock is loaded into the first bay level for Phase 1 processing. The residency time at each stage of processing is determined by an operations plan for composting. At step 805, the feedstock is agitated by dropping it through a chute to a lower bay level, at which time further moisturizing may be performed. At step 806, feedstock is loaded into offloading bay 112 by dropping it through a chute. At step 807, the feedstock is screened into finished compost and oversized feedstock material is recycled or discarded. At step 808, the finished compost is offloaded to trucks or other transportation for sale.

Hardware Architecture

For computer-implemented aspects, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 9:
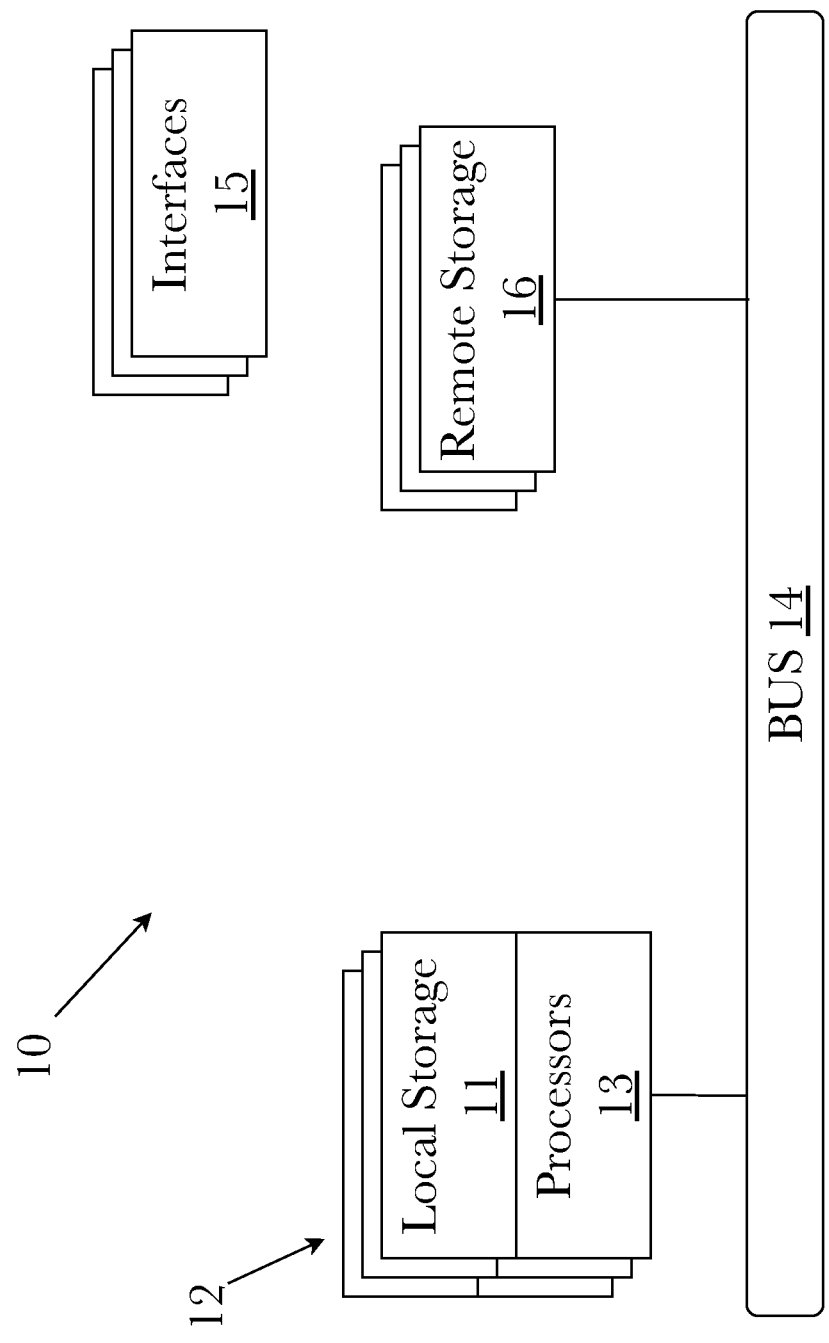
FIG. 9 is a block diagram illustrating an exemplary hardware architecture of a computing device.

Referring now to FIG. 9, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 9 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 maybe present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 10:
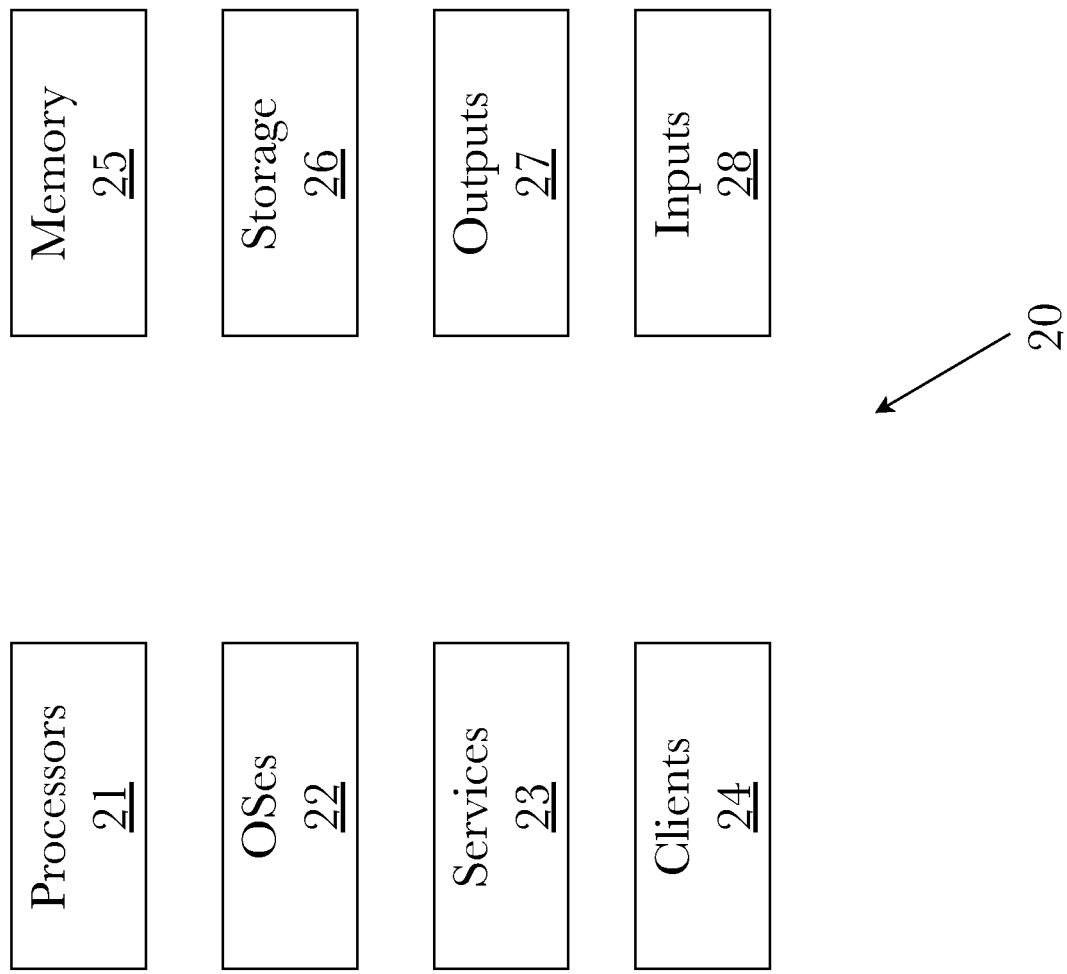
FIG. 10 is a block diagram illustrating an exemplary logical architecture for a client device.

In some aspects, systems may be implemented on a standalone computing system. Referring now to FIG. 10, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 maybe operable in system 20, and may be useful for providing common services to client applications 24. Services 23 may for example be WINDOWS™ services, userspace common services in a Linux environment, or any other type of common service architecture used with operating system 21. Input devices 28 maybe of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 9). Examples of storage devices 26 include flash memory, magnetic hard drive, CD-ROM, and/or the like.

Figure 11:
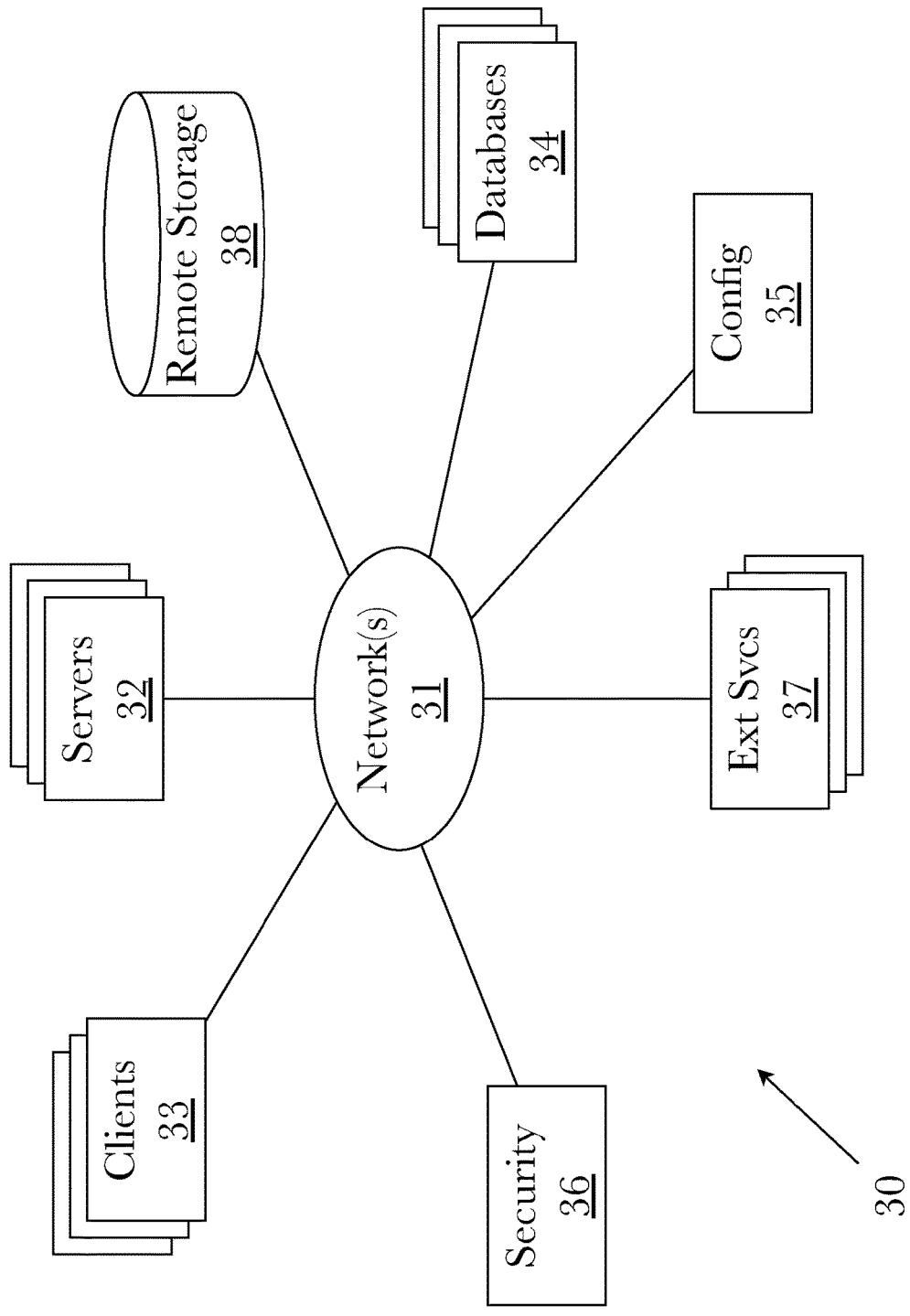
FIG. 11 is a block diagram showing an exemplary architectural arrangement of clients, servers, and external services.

In some aspects, systems may be implemented on a distributed computing network, such as one having any number of clients and/or servers. Referring now to FIG. 11, there is shown a block diagram depicting an exemplary architecture 30 for implementing at least a portion of a system according to one aspect on a distributed computing network. According to the aspect, any number of clients 33 maybe be provided. Each client 33 may run software for implementing client-side portions of a system; clients may comprise a system 20 such as that illustrated in FIG. 10. In addition, any number of servers 32 maybe provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 12:
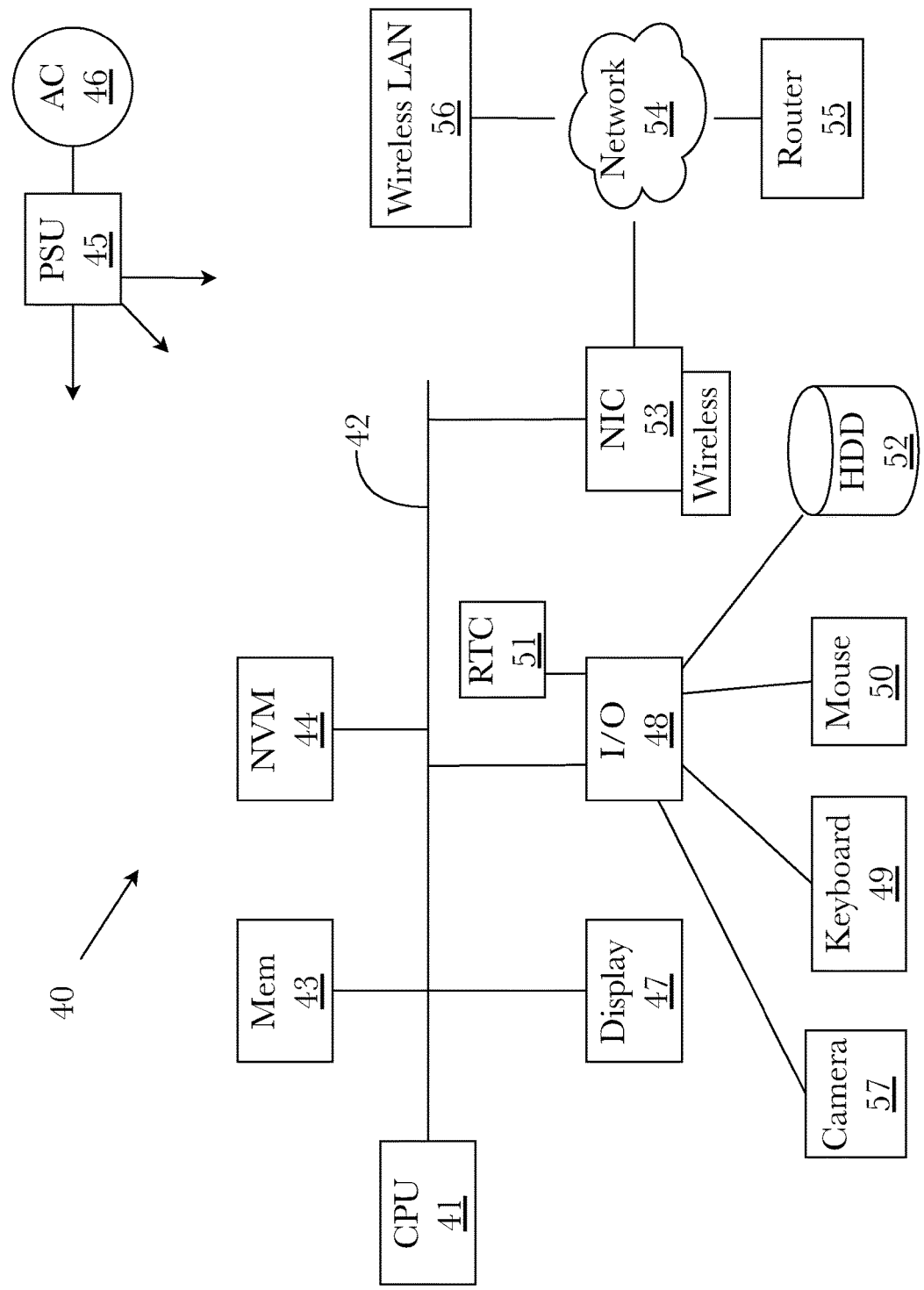
FIG. 12 is another block diagram illustrating an exemplary hardware architecture of a computing device.

FIG. 12 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A vertically-oriented composting facility comprising:
   a receiving and offloading level configured to receive feedstock for composting and allow for offloading of compost;
   one or more composting bay levels, each composting bay level comprising:
      one or more composting bins, each composting bin comprising:
         a bin loading area at a first end of the composting bin, configured to receive the feedstock via gravity from a transition chute located above the bin loading area;
         a transition chute opening at a second end of the composting bin into which feedstock may be dropped;
         a horizontal conveyor comprising an aerated floor and configured to convey the feedstock from the bin loading area to the transition chute opening;
         an aeration system comprising a first air pump configured to provide air flow under pressure to the feedstock through the aerated floor of the horizontal conveyor;
         a leachate collection system comprising piping configured to collect leachate from the feedstock which drains through the aerated floor of the horizontal conveyor; and
         an emissions collection system comprising:
            a second air pump configured to draw air from the bin and transfer it for emissions filtering; and
            a non-permeable cover or enclosure around the bin having an opening at either the first or second end of the bin and a connection to the second air pump at the other end, such that air within the enclosure is drawn across the bin from the opening to the second air pump.

2. The composting facility of claim 1, wherein the composting facility is constructed as a single structure.

3. The composting facility of claim 1, wherein one or more of the levels is a modular construction which can be stacked on top of other levels of the composting facility.

4. The composting facility of claim 1, wherein the composting facility is constructed as a hybrid structure comprising a single structure constructed on a ground surface, with one or more levels being modular construction stacked on top of the single structure or on top of other modular levels.

5. The composting facility of claim 1, wherein each of the one or more composting bay levels has a plurality of composting bins.

6. The composting facility of claim 1, wherein the horizontal conveyor is a moving floor.

7. The composting facility of claim 6, wherein aeration of the feedstock is provided by a dual-purpose aeration and leachate system comprising piping attached to one or more slats of the moving floor, the piping having risers extending up toward holes in the surface of the moving floor configured to both provide pressured air to the feedstock and receive leachate, wherein the aeration is provided by the first air pump connected to the piping via a flexible hose, and leachate drainage from the piping is provided by a flexible hose connected to a lower portion of the piping.

8. The composting facility of claim 1, wherein the horizontal conveyor is a porous belt or track.

9. The composting facility of claim 8, wherein aeration of the feedstock is provided by a dual-purpose aeration and leachate system comprising a collection pan or tray with a cover having holes for aeration and piping from the collection pan or tray, wherein the porous belt or track slides over the top of the cover and wherein holes, slits, or gaps in the conveyor belt or track periodically coincide with the holes in the cover, wherein the aeration is provided by the first air pump connected to the collection pan or tray and leachate is collected in the collection pan or tray and leachate drainage is provided by piping connected to a lower portion of the collection pan or tray.

10. The composting facility of claim 1, wherein turning of the feedstock is performed by dropping of the feedstock through the transition chute opening to a lower level of the composting facility, and wherein moisturization, or inoculation, or both are performed by sprayers as the feedstock drops to the lower level of the composting facility.

11. A vertically-oriented composting method comprising the steps of:
   receiving feedstock for composting at a receiving and offloading level of a vertically-oriented composting facility configured to receive feedstock for composting and allow for offloading of compost, the vertically-oriented composting facility comprising the receiving and offloading level and one or more composting bay levels, each composting bay level comprising one or more composting bins, each composting bin comprising a bin loading area, a transition chute opening, a horizontal conveyor, an aeration system, and a leachate collection system;
   for each composting bin of the one or more composting bins, performing the steps of:
      loading the feedstock to the bin loading area at a first end of the composting bin, the bin loading area configured to receive the feedstock via gravity from the transition chute located above the bin loading area;
      dropping the feedstock through the transition chute opening at a second end of the composting bin either to a composting bin at the next composting bay level down, or to the receiving and offloading level;
      conveying the feedstock from the bin loading area to the transition chute opening using a horizontal conveyor comprising an aerated floor;
      aerating the feedstock during conveyance using an aeration system comprising a first air pump configured to provide air flow under pressure to the feedstock through the aerated floor of the horizontal conveyor;
      collecting leachate from the feedstock using a leachate collection system comprising piping configured to collect leachate from the feedstock which drains through the aerated floor of the horizontal conveyor; and
      collecting emissions from the feedstock using an emissions collection system comprising:
         a second air pump configured to draw air from the bin and transfer it for emissions filtering; and
         a non-permeable cover or enclosure around the bin having an opening at either the first or second end of the bin and a connection to the second air pump at the other end, such that air within the enclosure is drawn across the bin from the opening to the second air pump.

12. The composting method of claim 11, wherein the method is applied on a vertical composting facility configured as a single structure.

13. The composting method of claim 11, wherein the method is applied on a vertical composting facility configured with one or more of the levels being a modular construction which can be stacked on top of other levels of the composting method.

14. The composting method of claim 11, wherein the method is applied on a vertical composting facility configured as a hybrid structure comprising a single structure constructed on a ground surface, with one or more levels being modular construction stacked on top of the single structure or on top of other modular levels.

15. The composting method of claim 11, wherein the method is applied on a vertical composting facility in which each of the one or more composting bay levels has a plurality of composting bins.

16. The composting method of claim 11, wherein the method is applied on a vertical composting facility having a moving floor as the horizontal conveyor.

17. The composting method of claim 16, further comprising the step of aerating the feedstock using a dual-purpose aeration and leachate system comprising piping attached to one or more slats of the moving floor, the piping having risers extending up toward holes in the surface of the moving floor configured to both provide pressured air to the feedstock and receive leachate, wherein the aeration is provided by the first air pump connected to the piping via a flexible hose, and leachate drainage from the piping is provided by a flexible hose connected to a lower portion of the piping.

18. The composting method of claim 11, wherein the method is applied on a vertical composting facility having a porous belt of track as the horizontal conveyor.

19. The composting method of claim 18, further comprising the step of aerating the feedstock using a dual-purpose aeration and leachate system comprising a collection pan or tray with a cover having holes for aeration and piping from the collection pan or tray, wherein the porous belt or track slides over the top of the cover and wherein holes, slits, or gaps in the conveyor belt or track periodically coincide with the holes in the cover, wherein the aeration is provided by the first air pump connected to the collection pan or tray and leachate is collected in the collection pan or tray and leachate drainage is provided by piping connected to a lower portion of the collection pan or tray.

20. The composting method of claim 11, further comprising the step of turning the feedstock by dropping of the feedstock through the transition chute opening to a lower level of the vertically-oriented composting facility, and moisturizing the feedstock, or inoculating the feedstock, or both, using by sprayers as the feedstock drops to the lower level of the composting method.

* * * * *